United States Patent [19]

Elliott et al.

[11] Patent Number: 5,030,562

[45] Date of Patent: Jul. 9, 1991

[54] METHOD FOR SCREENING BACTERIA AND APPLICATION THEREOF FOR FIELD CONTROL OF THE WEED DOWNY BROME

[75] Inventors: Lloyd F. Elliott, Bakersfield, Calif.; Ann C. Kennedy, Pullman, Wash.

[73] Assignee: The United States of America as represented by the Secretary of Agriculture, Washington, D.C.

[21] Appl. No.: 207,592

[22] Filed: Jun. 16, 1988

[51] Int. Cl.$^5$ ............................ C12Q 1/02; C12N 1/20
[52] U.S. Cl. ......................................... 435/29; 435/30; 435/34; 435/243; 435/803; 435/874; 435/253.3; 71/6
[58] Field of Search .................. 435/29, 32, 30, 34, 435/243, 803, 876, 877, 253.3; 47/58; 71/3, 6

[56] References Cited

U.S. PATENT DOCUMENTS

| | | | |
|---|---|---|---|
| 4,390,360 | 6/1983 | Walker | 71/79 |
| 4,419,120 | 12/1983 | Walker | 71/79 |
| 4,456,684 | 6/1984 | Weller et al. | 435/34 |
| 4,647,533 | 3/1987 | Weller et al. | 435/29 |

OTHER PUBLICATIONS

Bergey's Manual of Determinative Bacteriology, 8th ed, ed. R. E. Buchanan and N. E. Gibbons, The Williams & Wilkins Company, Baltimore (1974).
Bright, S. W. J. et al., "Selection in Vitro", in *Cereal Tissue and Cell Culture*, Martinus Nijhoff/Dr W. Junk Publishers, Boston, pp. 232-260 (1985).
C. A. Cherrington and L. F. Elliott, "Incidence of Inhibitory Pseudomonads in the Pacific Northwest," *Plant and Soil* 101(2): 159-165 (1987).
L. F. Elliott and J. M. Lynch, "Plant Growth-Inhibitory Pseudomonads Colonizing Winter Wheat (*Triticum aestivum* L.) Roots," *Plant and Soil* 84: 57-65 (1985).
D. C. Sands and A. D. Rovira, "Isolation of Fluorescent Pseudomonads with a Selective Medium," *Applied Microbiology* 20(3): 513-514 (1970).
M. J. Gasson, "Indicator Technique for Antimetabolic Toxin Production by Phytopathogenic Species of Pseudomonas," *Applied and Environmental Microbiology* 39(1): 25-29 (1980).
L. F. Elliott and J. M. Lynch, "Pseudomonads as a Factor in the Growth of Winter Wheat (*Triticum Aestivum* L.)," *Soil Biology and Biochemistry* 16: 69-71 (1984).
Bergey's Manual of Systematic Bacteriology, vol. 1, pp. 161-164, 163.
Ellis et al., "Persistence and Recovery of *Rhizobium japonicum* Inoculum in a Field Soil," *Agronomy Journal* 76: 573-576 (1984).
Jansen van Rensburg and Strijdom, "Competitive Abilities of *Rhizobium meliloti* Strains Considered to Have Potential as Inoculants," *Applied and Environmental Microbiology* 44: 96-106 (1982).
Weller, "Biological Control of Soilborne Plant Pathogens in the Rhizosphere with Bacteria," *Ann. Rev. Phytopathol.* 26: 379-407 (1988).
Henis, "Ecological Principles of Biocontrol of Soilborne Plant Pathogens: Trichoderma Model," In. *Current Perspectives in Microbial Ecology*, M. J. Klug and C. A. Reddy, ASM Press, Washington, D. C., pp. 353-361 (1988).

*Primary Examiner*—Esther L. Kepplinger
*Assistant Examiner*—Toni R. Scheiner
*Attorney, Agent, or Firm*—M. Howard Silverstein; John D. Fado; Margaret A. Connor

[57] ABSTRACT

A method for screening bacteria to select strains which inhibit the weed downy brome in small grain crops under field conditions and method for field application of the bacteria to inhibit downy brome in small grain crops in a commercial setting are described. Three Pseudomonas strains initially determined as nonfluorescent which passed the screen test are disclosed.

15 Claims, No Drawings

METHOD FOR SCREENING BACTERIA AND APPLICATION THEREOF FOR FIELD CONTROL OF THE WEED DOWNY BROME

BACKGROUND OF THE INVENTION

1. Field of the Invention

The invention relates to the isolation, selection, and application of novel strains of bacteria which have the ability to control the weed downy brome in small grain crops without deleteriously affecting the crop.

2. Description of the Art

Downy brome (*Bromus tectorum*) and the closely related species Japanese brome (*B. japonicus*), and cheat (*B. secalinus*), hereinafter referred to collectively as downy brome, are winter annual grass weeds which cause serious reductions in small grain crop yields by competing with crops for moisture, space, and nutrients. This results in significant economic losses. The spread of these weeds has increased in recent years because conservation tillage systems make these weeds more difficult to control than conventional tillage systems.

Downy brome is a major weed of winter crops especially winter wheat. It can also be a problem in winter barley but is of less economic importance because winter barley acreage is relatively small. Winter wheat yield losses can be as high as 45% with 84-100 downy brome weeds/yard$^2$ while losses of 10% occur with a reduced downy brome infestation (Stahlman, Kansas Agricultural Experiment Station 87-69-S, 1986). Downy brome control of greater than 80% with the herbicide dicloflop resulted in 129 to 263% increased grain yield when compared to the control (Thill et al. In: STEEP Conservation Concepts and Accomplishments, L. F. Elliott et al. (eds.), pages 275-287, Washington State University Press (1987)). However, no chemical herbicide presently available gives consistent control against this weed.

While use of antagonistic microorganisms for biological control of some weeds have been reported, no bacterial strain has been previously found which would control the weed downy brome; additionally, no procedure for the selection of bacteria which inhibit downy brome in small grain crops has been reported. Because the physiological characteristics required for a bacterial strain to control weeds are very specific as to (1) the weed to be controlled; (2) the mode of action of weed control; (3) the activity and ecological niche of the microorganism; and (4) cultural practices and soil and climatic conditions favorable for control, information about microorganism treatments for control of weeds other than downy brome cannot be used to predict strains of microorganisms which would reduce downy brome under field conditions or predict criteria for selecting such strains.

SUMMARY OF THE INVENTION

We have discovered a novel method for screening bacteria for selection of those strains which will inhibit (reduce the incidence or severity of) the growth of the weed downy brome in small grain crops under field conditions and a practical and effective method for application of the inhibitory bacteria to suppress downy brome growth in the field.

The bacteria selected by our method inhibit the growth of downy brome in small grain crops such as wheat, barley, and related crops without deleteriously affecting the crops. When applied as a spray or on straw, the novel bacteria obtained by our method have the ability to inhibit downy brome under field conditions.

By use of our method, we have also discovered three novel strains initially determined as non-fluorescent pseudomonads which are effective in inhibiting growth of downy brome in field grown wheat.

Our screening method comprises:

1. Isolating strains of bacteria having potential for inhibiting downy brome from (a) the rhizoplane (root surface) or rhizosphere (soil immediately surrounding the roots) or both rhizoplane and rhizosphere of downy brome plants or (b) the rhizoplane or rhizosphere or both rhizoplane and rhizosphere of the crop variety (or related crop variety) to be protected in the field.

2. Screening the bacterial strains isolated in step 1 in vitro by growing downy brome in agar in the presence of a cell culture, substantially cell-free culture supernatant, or cell-free culture filtrate of the isolate being tested; growing control downy brome in the same manner but without the addition of the cell culture, supernatant, or filtrate, and selecting as inhibitory bacteria those strains which inhibit downy brome as shown by reduction in root growth or reduction in germination when compared to the control. Those strains which inhibit downy brome are then tested in vitro against the small grain crop of the variety to be protected by growing the small grain crop in agar in the presence of a cell culture, substantially cell-free culture supernatant, or cell-free culture filtrate of the isolate being tested; growing control small grain crop plants in the same manner but without the addition of the cell culture, supernatant, or filtrate, and selecting those strains which do not deleteriously affect the growth of the small grain crop.

3. Subjecting the bacterial strains selected in step 2 to a first screening in soil by separately growing downy brome plants and the small grain crop of the variety to be protected in a growth chamber or greenhouse in the presence of the bacterial strain selected in step 2. The bacterial concentration used is that which maximizes the selection of the number of strains that have the potential to inhibit downy brome in the field without deleteriously affecting the crop to be protected from downy brome and minimizes the selection of field-ineffective strains; growing control downy brome and small grain crop plants in a similar manner but without the addition of the bacterial strain, and selecting as inhibitory bacteria those strains which inhibit downy brome as shown by reduction in root growth or reduction in shoot growth when compared to the control downy brome plants without deleteriously affecting the small grain crop to be protected.

4. Screening the bacterial strains selected in step 3 in the field by separately growing downy brome plants and the small grain crop to be protected in the field in the presence of the bacterial strain selected in step 3 in a concentration which maximizes the selection of the number of strains which have the potential to inhibit downy brome in the field without deleteriously affecting the crop to be protected from downy brome and minimizes the selection of field-ineffective strains; growing control downy brome and small grain crop plants in the same manner but without the addition of the bacteria, and selecting as field-inhibitory bacteria those strains that inhibit downy brome as shown by reduction in stand, reduction in root growth, or reduction in shoot growth when compared to the control plants without deleteriously affecting the small grain crop to be protected.

The bacterial strains selected by our method have the ability to inhibit downy brome in a commerical setting without deleteriously affecting the small grain crop to be protected when used as a treatment on the crop area to be protected. Such treatments include spraying an inhibitory amount of the selected bacteria or applying straw containing an inhibitory amount of the selected bacteria on the crop area after planting. Both methods are practical and economical for controlling downy brome growth in small grain crop stands. The former method is particularly suited to the crop growing in heavy residues, the latter to the crop growing in areas with little or no surface residues.

The need for a biological control of downy brome in cropland has long been recognized as crop losses due to this weed have been significant and control by herbicides impractical. By using the procedures and conditions of our screening method, strains of bacteria can be selected which will inhibit downy brome growth in the field. By using our application method, downy brome growth can be controlled in a commercial setting.

In accordance with this discovery, it is an object of the invention to provide a means for screening bacteria to select those strains which inhibit downy brome in small grain crops under field conditions without deleteriously affecting the small grain crop to be protected.

It is also an object of the invention to provide a method for biologically controlling downy brome in small grain crops under field conditions using the strains selected by our method.

Another object of the invention is the provision of a method to identify root colonizing non-fluorescent pseudomonads that inhibit downy brome and utilize the strong root colonizing ability of the organisms to establish on the roots of downy brome in the field. Similar to other bacterial strains, it is difficult to take these organisms from the growth chamber to the field due to variables such as soil conditions, soil moisture, temperature, and the like. By the use of our method, however, it is possible to assess bacteria for field effectiveness and to apply downy brome-inhibitory bacteria for control of downy brome in small grain crops.

Another object of the invention is the provision of novel strains initially determined as non-fluorescent pseudomonads which inhibit downy brome on field grown wheat without deleteriously affecting the wheat.

Other objects and advantages of the invention will become apparent from the ensuing description.

DESCRIPTION OF THE PREFERRED EMBODIMENTS

The screening method comprises:

Step 1. Isolation of Strains of Potentially Inhibitory Bacteria

To biologically control downy brome, a bacterial strain must have the ability to establish and grow in the microhabitat where it is to be used to inhibit the growth of the weed. This means it must have the ability to colonize the root system of downy brome. For the purposes of this invention, the term "downy brome" as used herein includes three closely related species of the genus Bromus, downy brome (*Bromus tectorum*), Japanese brome (*B. japonicus*), and cheat (*B. secalinus*). Such bacteria are selected by isolating strains from the rhizoplane (root surface) or rhizosphere (soil immediately surrounding the roots) or both rhizoplane and rhizosphere of (a) downy brome plants or (b) small grain crops. Although strains from the rhizoplane or rhizosphere of one species of downy brome or one small grain may be isolated in this step for potential use to control another species of downy brome or another small grain crop, it is preferred that the bacterial strain be isolated from the species of downy brome to be inhibited or from the variety of small grain to be protected as it is likely to best function in the ultimate biocontrol habitat.

It is within the compass of the invention to isolate any type of bacteria having the potential to inhibit downy brome without deleteriously affecting the small grain crop to be protected, however non-fluorescent pseudomonads are the bacteria of choice because (1) they can be easily isolated, cultured, and identified; (2) they normally inhabit rhizosphere or rhizoplane soil, (3) they are nutritionally versatile, being able to utilize a large number of organic substrates, including, root exudates, (4) some strains produce toxins that inhibit downy brome; and (5) they can be successfully introduced into the root system of small grain crops and become established in the rhizosphere and rhizoplane.

Winter wheat is the small grain crop which is most significantly affected by downy brome by reduction in crop yield and resultant economic loss. For the purposes of description of our method, winter wheat is used as exemplary of the crop to be protected, however, our method is applicable to other small grains crops, for example, barley, oats, rye, triticale, and related crops.

The isolation procedure is as follows: winter wheat plants or downy brome plants are dug from the field and adhering soil gently washed from the roots with flowing tapwater. The roots are excised from the tops. The bacteria are collected and isolated by standard procedures. For example, bacteria of the genus Pseudomonas can be isolated by placing the excised roots in sterile dilutions blanks containing sterile water and glass beads and shaking the mixture vigorously to remove organisms clinging to the root surface. Then serial dilutions are prepared and spread plated on to a Pseudomonas selective medium such as King's Medium B supplemented with novobiocin, penicillin, and cycloheximide (KMB NPC) (Sands and Rovira, *Applied Microbiology* 20:513–514 (1970)), and incubated at a suitable temperature, e.g., 20° C. Individual non-fluorescent colonies are identified by viewing the plates under ultraviolet light and selecting those colonies that do not exhibit fluorescence. For short term storage during the screening procedure, inoculum from individual non-fluorescent colonies is placed on a KMB NPC slant.

Step 2. Screening of the Bacterial Strains In Vitro

Bacterial strains isolated in step 1 are screened to select those strains which inhibit downy brome growth in vitro as exhibited by reduction in root growth or germination as compared to control plants. Those strains which are inhibitory to downy brome are then tested against wheat; those strains which do not deleteriously affect wheat growth in vitro are selected.

In the in vitro screening procedure, individual non-fluorescent colonies are inoculated into a medium suitable for growing up the colonies, for example, Pseudomonas minimal salts medium (PMS) described by Gasson, *Applied and Environmental Microbiology* 39: 25–29

(1980), and grown at at a suitable temperature, e.g., about 20° C. until late logarithmic growth (about $10^9$ to $10^{11}$ cells per ml culture medium). The cells are then treated in at least one of the following ways: (1) the culture is used directly, (2) the culture is centrifuged to obtain a substantially cell-free culture supernatant (not more than about $10^4$ cells per ml of supernatant), or (3) the cell culture is centrifuged and filter sterilized to obtain a cell-free culture filtrate (no cells present). The first method assays both the effect of the organism and the effect of toxin production by the organism on downy brome growth. The second method is a quick assay to determine the effect of toxin production by the organism on the growth of downy brome. The third method assays only the effect of toxin production by the organism on downy brome growth. We have found that the assays for toxin production appear to provide for better selection of effective strains.

Downy brome growth inhibition is assessed by adding to petri plates a standard quantity, usually 2 ml, of the cell culture, substantially cell-free culture supernatant, or cell-free culture filtrate. A standard quantity, usually 18 ml, of 0.9% molten agar (50° C.) is added to each plate, the contents mixed, and allowed to solidify. Generally two plates are prepared for each organism tested. Control plates are prepared by using PMS instead of the cell culture, substantially cell-free culture supernatant, or cell-free culture filtrate. The plates are planted with pregerminated downy brome seeds, 15 seeds per plate is convenient, and allowed to grow at a suitable temperature, e.g., 15° C. Before root growth from the seedlings interferes with each other, about 3–6 days, the seedlings are pulled from the agar and root length or germination or both are recorded. The organisms showing significant inhibition of downy brome growth (length) or germination when compared to the control are tested against winter wheat seedling growth. For the purposes of this invention, significant inhibition of downy brome in the in vitro test is defined as at least a 50% reduction in root growth (length) when compared to the control or at least a 20% reduction in germination when compared to the control.

The strain selected above is assessed against wheat as follows: Test tubes receive a standard quantity, usually 1 ml each, of the cell culture, substantially cell-free culture supernatant, or the cell-free culture filtrate which was used in the downy brome test, and a standard quantity of 0.9% molten agar (50° C.), usually about 9 ml, is added to each tube, the contents mixed, and the tube slanted. Generally 10 growth tubes are prepared for each organism tested. Control tubes are prepared identically except that PMS is substituted for the cell culture, substantially cell-free culture supernatant, or the cell-free culture filtrate. When solidified, pregerminated winter wheat seeds (one per tube) are planted mid-slope on the slants and allowed to grow at a suitable temperature, e.g., 15° C. Before root growth reaches the bottom of the tube, approximately 3–6 days, the seedlings are pulled from the growth tubes and root length recorded. A bacterial strain is denoted as one that does not deleteriously affect winter wheat when root growth reduction of the bacterial treated wheat is less than 10% when compared to the control wheat seedlings.

Pure cultures of the strains significantly inhibiting downy brome growth with little or no effect on winter wheat growth are individually streaked onto a suitable medium such as KMB NPC and selected and restreaked until the strain is pure and stable. Each individual strain is grown up and maintained so as to keep it stable such as by storing in glycerol at −10° C. or lyophilizing and storing at −10° C.

Step 3. Screening of the Bacterial Strains in the Growth Chamber

Bacterial strains isolated in the step 2 are subjected to a first screening in soil by separately growing downy brome plants and wheat plants in a growth chamber or greenhouse in the presence of the bacterial strain selected in step 2. In this step, those strains are selected which, at a particular concentration, inhibit downy brome without deleteriously affecting wheat.

In this test, pots are filled with soil and seeded with downy brome or with wheat seeds. We have found that 6.4 cm diameter by 7.6 cm deep plastic pots seeded with 10 downy brome seeds and 7.6 cm diameter by 15.2 cm deep plastic pots seeded with four winter wheat seeds are convenient sizes for growth chamber or greenhouse studies. Any soil suitable for growth chamber studies can be used. One exemplary soil is Ritzville silt loam amended with 20% sand by weight. It is not necessary to surface-sterilize the seeds prior to planting.

The amount of bacteria per downy brome seed in the test pots is selected so as to optimize the selection of field-effective strains and minimize the selection of field-ineffective strains. For non-fluorescent pseudomonads, we have found that a range of $10^8$ to $10^{10}$ colony forming units (CFU) of the test strain per downy brome test pot is applied to the soil surface. One convenient method is putting the test strain in a liquid such as distilled water or PMS and dripping the liquid on to the soil surface. Wheat seeds are grown in the presence of $10^8$ to $10^{10}$ CFU of the test strain per pot with 4 seeds to assess the effect of the bacteria on wheat. Separate downy brome and winter wheat controls are prepared identical to the test samples except without bacterial treatment.

The soil is wetted to provide good plant growth, and the pots incubated in the growth chamber. We have found that a 14-hour day at 18° C. and a 10-hour night at 13° C. is suitable. After about 3 to 4 weeks, the downy brome and wheat seedlings are pulled up and the roots washed with water until free of soil. The roots and shoots of the downy brome and wheat seedlings are excised and roots or shoots or both dried to remove water so that a comparison to control plants can be made. Drying at 60° C. for 48 hours is suitable.

Evaluation of Seedlings in the Growth Chamber Test

To evaluate the bacterial treatment, root or shoot dry weight of the downy brome plants is compared with the root or shoot dry weight of the control downy brome plants. Bacterial strains which cause the treated downy brome seedlings to have reduced root growth (reduced root dry weight when compared to the control) of at least 25% or which cause the treated downy brome seedlings to have reduced shoot growth (reduced shoot dry weight when compared to the control) of at least 25% are considered inhibitory to downy brome in this test. While reduction in germination of downy brome compared with the control is not necessary, we have found that the additional criterion of selecting strains which showed a 20% or greater reduction in germination useful. To obtain germination values, emergence of downy brome grown in the presence of the test strain is counted and compared with the control plants.

To evaluate the bacterial treatment on wheat, root dry weight or shoot dry weight of the wheat plants are compared with the control wheat plants. For the purposes of this invention, a bacterial strain is denoted as one that does not deleteriously affect winter wheat when reduction in root growth (root dry weight) or shoot growth (shoot dry weight) of the bacterial treated wheat is less than 10% when compared to the control wheat seedlings.

Step 4. Screening the Bacterial Strains in the Field

Bacterial strains selected in the previous step are next tested in the field. Treatment and control plots are laid out. We have found that treatment plots consisting of a meter$^2$ are suitable. The control (non-treatment) should be within close proximity to the comparable treatment plot so that treatment and non-treatment plots have similar soil conditions.

For the field test, it is preferred that downy brome plants be grown in plots that are substantially free of other weeds so that variability due to the presence of other weeds is reduced. This can be accomplished by chemical herbicide application or fumigation prior to planting. We have found it useful to have the previous crop residues of the small grain crop, e.g., barley or wheat, left on the soil surface as this provides a substrate for the inoculum. A convenient plot size is four 1-meter rows of downy brome per treatment with a control plot within about 6 meters of the treatment plot. The plots are seeded to downy brome, about 70 to 150 seeds per meter$^2$. Individual bacterial strains to be tested are applied to the soil as a spray treatment or on straw. The treatment is applied just after planting to up to 4 weeks. The spray treatment is economical and more convenient; straw provides protection for inoculum under adverse weather conditions. For the spray treatment, the test strain in a liquid such as distilled water or PMS is sprayed on to the soil to provide a concentration of about $10^7$ to $10^{12}$ and preferably about $10^8$ CFU of the test strain per meter$^2$. The straw treatment is prepared by placing straw chopped into about 5 cm lengths into a tank and inoculating with the strain being tested. Water potential of the straw is adjusted to provide good growth of the organism. Thereafter, the straw is mixed about once a day. After about 5 days at about 15°–20° C., the bacteria ranges about $10^9$ to $10^{10}$ CFU of the test strain per gram of straw. Straw is added to the plots to give about $10^7$ to $10^{12}$, and preferably about $10^8$ CFU of the test strain per meter$^2$. Control plots are treated identical to the test plot except that no bacteria are applied. To have statistical significance, each organism treatment is replicated a minimum of three times.

Plots seeded to winter wheat (about 100 to 150 seeds per meter$^2$) are seeded beside the downy brome plots and the test organisms are sprayed on to the plots to provide a concentration of about $10^7$ to $10^{12}$, and preferably about $10^8$ CFU of the test strain per meter$^2$. A convenient plot size is a meter$^2$. The treatment is applied just after planting to up to 4 weeks after planting. The control plants receive identical treatment except that no bacteria are applied. To have statistical significance, each organism treatment is replicated a minimum of three times.

Evaluation of Seedlings in the Field Test

To assess the effect of the bacterial treatment in the inhibition of downy brome in the field, after adequate growth has occurred, e.g., about the 5-leaf stage, the downy brome plants are harvested, roots washed, and at least one of the following is obtained: root dry weight, shoot dry weight, or stand (numbers of plant per meter length). Bacterial strains which cause the treated downy brome plants to average a reduction in root growth (root dry weight), reduction in shoot growth (shoot dry weight), or reduction in stand of at least 10% when compared to control downy brome plants are considered inhibitory to downy brome in the field test. To assess the effect of the bacterial treatment on winter wheat, it is harvested, roots washed, and at least one of the following is obtained: root dry weight, shoot dry weight, or stand (numbers of plant per meter length). Those bacterial strains which cause winter wheat to average less than 10% reduction in root growth (root dry weight), shoot growth (shoot dry weight) or stand compared to control wheat are defined as not deleteriously affecting the crop.

Application of Downy Brome-Inhibitory Bacteria For Control of Downy Brome in a Commercial Setting For convenience or economy of application, one of two methods is useful to control downy brome in a commercial setting depending on whether the field has surface residues or bare soil. The inhibitory organisms grow well in straw; if it is desired to control downy brome in wheat sown into previous crop residues on the soil surface, spraying the organisms on the residues may be the most convenient method of application. It is best to spray after a rain or shortly before and during periods of high rain probability. Where prolonged hot-dry periods may occur, application of inoculated straw or similar material may give better results. Application of the organisms in either case should be done after seeding up to 4 weeks after seeding.

Individual strains of bacteria which inhibited downy brome in the growth chamber and field tests without deleteriously affecting wheat are cultured by standard methods for a time to grow sufficient bacteria to treat the field area, generally about 48 hours for spray treatments or for about 5 days on straw or similar material for straw treatment. After wheat is seeded into the field, the organisms are applied to the field in an amount sufficient to inhibit downy brome. For non-fluorescent pseudomonads, this amount is about $10^7$ to $10^{12}$ CFU of inhibitory bacteria per meter$^2$.

Statement of Deposit. Strains initially determined as non-fluorescent pseudomonads that passed the above screening test have been deposited in the Agricultural Research Culture Collection (NRRL) in Peoria, Ill. 61604 and have been assigned the following accession numbers: NRRL B-18293, NRRL B-18294, and NRRL B-18295.

EXAMPLES

The following examples are intended only to further illustrate the invention and are not intended to limit the scope of the invention which is defined by the claims.

Example 1

Isolation of Pseudomonas Strains

Winter wheat and downy brome plants were dug from the field and the roots washed free from adhering soil in flowing tapwater. The roots were excised and placed in a sterile dilution blank containing 95 ml of deionized water and glass beads. The mixture was vigorously shaken on a wrist-action shaker and serial dilutions prepared and spread plated on King's Medium B supplemented with 45 mg novobiocin, 45 mg penicillin G, and 75 mg cyclohexamide (Sands and Rovira, supra). Non-fluorescent pseudomonads were identified by viewing the plates under ultraviolet light after 2–3 days of incubation at 20° C.

Example 2

Initial Isolate Screening.

Individual non-fluorescent colonies obtained by the procedure outlined in Example 1 were screened in vitro as follows: Individual isolates were grown in PMS broth (Gasson, supra, KCl, 0.2 g; $NH_4H_2PO_4$, 1.00 g; $H_2O$, 100 ml; adjusted to pH 7.0, after autoclaving 20 ml sterile 2% $MgSO_4.7H_2O$, and 20 ml sterile 10% glucose added) at 20° C. until late logarithmic growth (0.9 O.D. at 500 nm on the spectrophotometer). The cultures were then used to inoculate the downy brome assay directly, centrifuged to obtain a substantially cell-free culture supernatant, or centrifuged and filter sterilized to obtain a cell-free culture filtrate.

Plastic petri dishes received 2 ml each of the cell culture, substantially cell-free culture supernatant, or the cell-free culture filtrate. Control plates received 2 ml of fresh PMS. Then 18 ml of 0.9% molten bacto-agar (Difco) (50° C.) were added to each plate, and the contents mixed. When solidified, 15 pregerminated downy brome seeds were planted on each plate and allowed to grow at 15° C. Before root growth from the seedlings interfered with each other (5 days), the seedlings were pulled from the agar and root and shoot length were recorded. The organisms which showed at least a 50% reduction in root growth when compared to the control were denoted as inhibitory to downy brome and were tested against winter wheat seedling growth. Test tubes received 1 ml each of the cell culture, substantially cell-free culture supernatant, or the cell-free culture filtrate. Control tubes received 1 ml of fresh PMS. Then 9 ml of 0.9% molten bacto-agar (50° C.) were added to each tube, the contents mixed, and the tubes slanted. When solidified, a pregerminated wheat seed was planted mid-slope on each slant and allowed to grow at 15° C. Before root growth reached the bottom of the tube (3 days), the seedlings were pulled from the growth tubes and root and shoot length recorded. In order for the bacterial strain to be considered not to be deleterious to winter wheat, the wheat seedlings treated with the bacteria must have averaged less than 10% reduced root growth when compared to the control plants.

Over 300 non-fluorescent Pseudomonas have been tested for inhibition of downy brome growth. Of these, about six strains have shown strong inhibition of downy brome growth with no effect on winter wheat growth. The test results for three strains which passed the in vitro screening test are given in Table 1. Cultures retained for further studies were individually streaked and selected and restreaked until the strain was pure and stable and stored in sterile aqueous glycerol at −10° C.

TABLE 1

| Isolate | Downy Brome | | Winter Wheat | |
|---|---|---|---|---|
| | Root Length (mm) | Reduction In Root Growth Compared to Control (%) | Root Length (mm) | Reduction In Root Growth Compared to Control (%) |
| Control | 8.8 | — | 33.2' | — |
| NRRL B-18293 | 2.4 | 73 | 37.8 | None |
| NRRL B-18294 | 1.8 | 80 | 43.5 | None |
| NRRL B-18295 | 3.2 | 64 | 35.3 | None |

Example 3

Screening of Bacterial Strains in the Growth Chamber

Non-fluorescent Pseudomonas strains NRRL B-18293, NRRL B-18294, and NRRL B-19295 that were inhibitory to downy brome but not deleterious to wheat as described in Example 2 were screened in the growth chamber to determine the effect of the isolates on test plants grown in soil. Ten downy brome (B. tectorum) seeds were seeded into 6.4 diameter by 7.6 cm deep plastic pots filled with Ritzville silt loam plus 20% sand (w/w), and four winter wheat seeds were seeded into 7.6 cm diameter by 15.2 cm deep plastic pots filled with Ritzville silt loam with 20% fine sand (w/w). Approximately $10^8$ CFU of inhibitory pseudomonads NRRL B-18293, NRRL B-18294, or NRRL B-18295 were dripped on the soil surface on the seeded area in the downy brome and winter wheat seeded pots. Controls received the fresh medium without cells. Four replicates of each treatment were included. The soil was wetted to $-\frac{1}{3}$ bar water potential, and the pots incubated in the growth chamber with a 14-hour day at 18° C. and a 10-hour night at 13° C.

Seedling emergence was determined. After 2 weeks the seedlings were pulled up and the roots washed with water until free of soil. The roots and shoots were excised, dried at 60° C. for 48 hours, and dry shoot and root weight recorded. In order for the bacterial strain to be considered to be inhibitory to downy brome without deleteriously affecting wheat, the downy brome seedlings treated with the bacteria must have averaged at least 25% reduced root growth (dry root weight) when compared to control downy brome seedlings, and the winter wheat seedlings treated with the bacteria must have averaged less than 10% reduced root growth (dry root weight) when compared to control wheat seedlings. The test results for the strains are given in Table 2. As can be seen from the data, the strains passed the growth chamber test.

TABLE 2

| Isolate | Downy Brome | | Winter Wheat | |
|---|---|---|---|---|
| | Root wt/pot (mg) | Reduction In Root Growth Compared to Control (%) | Root wt/plant (mg) | Reduction In Root Growth Compared to Control (%) |
| Control | 37.5 | — | 29.0 | — |
| NRRL B-18293 | 24.0 | 36 | 40.3 | None |
| NRRL B-18294 | 27.3 | 27 | 41.3 | None |
| NRRL B-18295 | 17.0 | 55 | 31.0 | None |

Example 4

Field Screening of Bacteria to Inhibit Downy Brome Growth

Strains NRRL B-18293 and NRRL B-18294 that had passed the growth chamber test were field tested in Pendleton, Oreg. during the 1987–1988 growing season as follows: PMS broth was inoculated with glycerol-preserved-strains and incubated at 20° C. for 2 days. Agar plates of PMS medium were prepared and each inoculated with 1 ml of the PMS broth culture medium containing the individual strains. One ml of inoculum was spread on the plate with a sterile glass rod. A sufficient number of plates were inoculated to provide organisms to seed the field plots at $10^9$ CFU of the test strain/$m^2$. The plates were incubated at 15° C. for 3 days to obtain maximum growth. The plates were flooded with sterile deionized water, and the organisms mixed in the water by agitation of the surface of the plate with a glass rod. The plate washings for each strain were pooled. The suspension was diluted with sterile deionized water to an optical density of 0.9 (determined on a spectrophotometer at 600 nm). The amount of this solution necessary to treat the plot area was added to a sprinkling can (about 7 liter capacity) and water added to fill the can to facilitate even spreading of the organisms on the plot. For example, for a plot of 1 $m^2$, the amount of the solution necessary to contain about $10^9$ CFU of the test strain/$m^2$ was added to the sprinkling can.

The field had naturally occurring residue on it. The plots were fumigated with methyl bromide prior to planting to remove ambient weed seeds. Plots were 1 meter$^2$ with 1 meter between plots were arranged in a randomized complete block design. Each treatment was replicated four times (sprinkled with the test strain or a water-check). Before the organisms were added, the plots were hand seeded in rows onto the soil surface with downy brome (*B. tectorum*) with 10 seeds planted per 25 cm. Then the organisms or water treatments were sprinkled on.

Another set of identical plots as described above were established with the only difference being the mode of application of the bacteria being tested. Inoculum of each test strain was prepared as described previously incubating in PMS broth. Chopped straw, about 5 cm lengths, was placed in a plastic container and wetted to about $-\frac{1}{3}$ bar water potential. Then 1 ml of the PMS inoculum of each test strain or of sterile PMS broth per 100 g of straw was added (each to a separate container of straw) and mixed. Extreme care was taken to avoid contamination from one vessel to the other. The mixtures were incubated at ambient temperatures usually ranging from 22° C. during the day to about 12° C. during the night. After 5 days, counts of the applied microorganism were greater than about $10^9$ CFU per gram of straw dry weight. This was the amount desired to treat a $m^2$ of plot. The quantity of straw is too small to readily spread evenly over the plots so it was mixed with 49 g of fresh straw to facilitate spreading, and the straw plus organisms were added at a rate to give $10^9$ CFU per $m^2$ of plot. The organisms plus straw or the straw control was applied to an identical set of plots in the same configuration as described above for organisms in water or water check treatments.

In early April, a 0.3 m of the middle row from each downy brome plot was carefully dug so no roots were lost. The roots were carefully washed under flowing tap water to remove all visible soil. Tops and roots from the downy brome were excised and dried at 60° C. for 48 hours. In order for the bacterial strain to be considered inhibitory to downy brome in the field test, the downy brome plants treated with the bacteria must average at least 10% reduced stand, at least 10% reduced root growth (root dry weight), or at least 10% reduced shoot growth (shoot dry weight) when compared to the control downy brome plants. Table 3 shows the inhibition of downy brome by non-fluorescent strains NRRL B-18293 and NRRL B-18294 sprayed on the residue and soil surface (Spray) or incubated with straw before applying to the soil surface (Straw). As can be seen from the data, the strains passed the field test.

Winter wheat was grown in field plots and treated with strains NRRL B-18293 and NRRL B-18294 at $10^9$ CFU per meter$^2$ showed no difference in stand count from control winter wheat, thereby showing that neither of the test strains deleteriously affected winter wheat.

TABLE 3

| Treatment Organism | Plant Number (#/0.3 m) | % Reduction in Plant Number Compared to Control | Root Dry Wt. (g/0.3 m) | % Reduction in Root Growth Compared to Control | Shoot Dry Wt. (g/0.3 m) | % Reduction in Shoot Growth Compared to Control |
|---|---|---|---|---|---|---|
| SPRAY | | | | | | |
| Control | 18.2 | — | 6.02 | — | 26.87 | — |
| NRRL B-18293 | 12.5 | 31 | 4.24 | 29 | 15.58 | 42 |
| NRRL B-18294 | 18.5 | None | 4.95 | 18 | 27.93 | None |
| STRAW | | | | | | |
| Control | 20.5 | — | 5.56 | — | 28.03 | — |
| NRRL B-18293 | 16.2 | 21 | 4.60 | 17 | 20.20 | 28 |
| NRRL B-18294 | 17.5 | 15 | 5.15 | 7 | 21.56 | 23 |

In another field test NRRL B-18295 was tested as described above for the other strains. Downy brome plants treated with this strain averaged reduced stand and reduced shoot growth (shoot dry weight) of 35% and 45%, respectively, compared to control downy brome plants. Winter wheat treated with this strain showed no reduction in stand or shoot growth compared to control winter wheat.

It is understood that the foregoing detailed description is given merely by way of illustration and that modification and variations may be made therein without departing from the spirit and scope of the invention.

Having thus described our invention, we claim:

1. A method for screening bacteria to select strains which will inhibit downy brome growth in field grown small grain crops without deleteriously affecting the small grain crop, which comprises:

(a) isolating a strain of bacteria from the rhizoplane, rhizosphere, or both rhizoplane and rhizosphere of downy brome or a small grain crop grown in the field;
(b) screening said strain isolated in step (a) for inhibition of downy brome growth without deleteriously affecting the small grain crop in vitro as follows:
  (1) growing downy brome in vitro in the presence of a cell culture of said strain isolated in step (a), a substantially cell-free culture supernatant obtained from said strain, or a cell-free culture filtrate obtained from said strain isolated in step (a);
  (2) growning downy brome as in step (b) (1) without the addition of said cell culture of said strain, said culture supernatant, or said culture filtrate;
  (3) selecting a strain which caused downy brome of step (b) (1) to average at least a 50% reduction in root growth or at least a 20% reduction in germination compared to downy brome grown in step (b) (2);
  (4) growing the small grain crop of the variety to be protected in vitro in the presence of a cell culture of said strain isolated in step (b) (3), a substantially cell-free culture supernatant obtained from said strain, or a cell-free culture filtrate obtained from said strain isolated in step (b) (3);
  (5) growing said small grain crop of the variety to be protected as in step (b) (4) without the addition of said cell culture of said strain, said culture supernatant, or said culture filtrate;
  (6) selecting a strain which caused said small grain crop of step (b) (4) to average less than 10% reduction in root growth compared to said small grain crop grown in step (b) (5);
(c) screening said strain selected in step (b) (6) for inhibition of downy brome without deleteriously affecting the small grain crop in a growth chamber as follows:
  (1) separately growing downy brome and the small grain crop of the variety to be protected in the growth chamber in the presence of said strain selected in step (b) (6) in a concentration of about $10^8$ to $10^{10}$ CFU of said strain per 10 downy brome seeds and in a concentration of about $10^8$ to $10^{10}$ CFU of said strain per 4 small grain crop seeds;
  (2) growing downy brome and said small grain crop as in step (c) (1) without the addition of said strain; and
  (3) selecting a strain which caused downy brome of step (c) (1) to average at least a 25% reduction in root growth or at least a 25% reduction in shoot growth compared to downy brome grown in step (c) (2) and which caused said small grain crop grown in step (c) (1) to average less than 10% reduction in root growth or shoot growth compared to said small grain crop grown in step (c) (2);
(d) screening said strain selected in step (c) (3) for inhibition of downy brome without deleteriously affecting the small grain crop in the field as follows:
  (1) separately growing downy brome and the small grain crop of the variety to be protected in the field in the presence of said strain selected in step (c) (3) in a concentration of about $10^7$ to $10^{12}$ CFU of said strain per meter$^2$ of said downy brome and said small grain crop;
  (2) growing downy brome and said small grain crop as in step (d) (1) without the addition of said strain; and
  (3) selecting a strain which caused downy brome of step (d) (1) to average at least a 10% reduction in stand, root growth, or shoot growth compared to downy brome grown in step (d) (2) and which caused said small grain crop grown in step (d) (1) to average less than 10% reduction in stand, root growth, or shoot growth compared to said small grain crop grown in step (d) (2).

2. The method of claim 1, further comprising:
(e) applying said strain of bacteria selected in step (d) (3) to field grown small grain crops of the variety to be protected in an amount sufficient to inhibit the growth of downy brome in said crop.

3. The method of claim 2 wherein said strain is applied in a concentration of about $10^7$ to $10^{12}$ CFU per meter$^2$.

4. The method of claim 3 wherein said strain is applied as a spray treatment comprising said strain in a liquid carrier.

5. The method of claim 3 wherein said strain is applied as a straw treatment comprising said strain grown on straw.

6. The method of claim 1 wherein said downy brome is *Bromus tectorum*.

7. The method of claim 1 wherein said small grain crop is winter wheat.

8. The method of claim 2 wherein said downy brome is *Bromus tectorum* and said small grain crop is winter wheat.

9. A method of inhibiting the growth of downy brome in small grain crops grown in the field, which comprises growing the small grain crop of the variety to be protected in the presence of an inhibitory amount of a biologically pure culture of a bacteria which inhibits downy brome in said small grain crop under field conditions as determined by passing the screen test of claim 1.

10. The method of claim 9 wherein said biologically pure culture of said bacteria comprises a strain of Pseudomonas.

11. The method of claim 10 wherein said biologically pure culture of said bacteria comprises a strain of non-fluorescent Pseudomonas.

12. The method of claim 10 wherein said strain of Pseudomonas is selected from the group consisting of NRRL B-18293, NRRL B-18294, and NRRL B-18295.

13. A biologically pure culture of bacteria which is endogenous to the rhizosphere or rhizoplane of downy brome or a small grain crop and which inhibits downy brome in small grain crops under field conditions as determined by passing the screen test of claim 1 wherein said culture comprises a strain of Pseudomonas.

14. The biologically pure culture of claim 13 wherein said culture comprises a strain of non-fluorescent Pseudomonas.

15. A biologically pure culture of bacteria which inhibits downy brome in small grain crops under field conditions as determined by passing the screen test of claim 1 wherein said culture comprises a strain of Pseudomonas selected from the group consisting of NRRL B-18293, NRRL B-18294, and NRRL B-18295.

* * * * *